United States Patent
Jones

Patent Number: 5,083,575
Date of Patent: Jan. 28, 1992

[54] CHILD'S SECTIONED I.V. BOARD

[76] Inventor: Hedwig E. Jones, 3519 Gemini Ct., Concord, Calif. 94519

[21] Appl. No.: 754,040

[22] Filed: Sep. 3, 1991

[51] Int. Cl.⁵ ............................................. A61F 5/37
[52] U.S. Cl. ................................. 128/877; 128/869; 128/846
[58] Field of Search ................ 128/68, 77, 845, 846, 128/869, 877, 878, 879, 880, 165

[56] References Cited

U.S. PATENT DOCUMENTS

| | | | |
|---|---|---|---|
| 2,693,794 | 11/1954 | Neville | 128/877 X |
| 3,256,880 | 6/1966 | Caypinar | 128/877 |
| 3,421,500 | 1/1969 | Jacobson | 128/77 UX |
| 3,724,456 | 4/1973 | Waxman | 128/877 |
| 3,812,851 | 5/1974 | Rodriguez | 128/877 |
| 3,818,905 | 6/1974 | LeBold | 128/77 |
| 4,928,712 | 5/1990 | Mele | 128/877 |
| 5,003,997 | 4/1991 | Stewart et al. | 128/879 X |
| 5,025,801 | 6/1991 | Callaway | 128/877 |

Primary Examiner—Robert A. Hafer
Assistant Examiner—Sam Rimell

[57] ABSTRACT

An I.V. board in two sections that allows the hand section to be put on first and secured by a snap-on cover, making it possible to bend the hand at the wrist while it is immobilized for starting an I.V. The hand section also features an opening in the center for the insertion of a light, if needed to locate a vein. Once the I.V. is started and secured, the arm section is added and attached with VELCRO-closing armbands making the use of tape unnecessary.

5 Claims, 1 Drawing Sheet

CHILD'S SECTIONED I.V. BOARD

BACKGROUND OF THE INVENTION

1. Field of the Invention

The invention relates generally to a device that will immobilize a child's hand while an intravenous infusion is started and keep it immobilized throughout the life of the infusion. Such a device is generally referred to as an I.V. board, I.V. being the accepted abbreviation for an intravenous infusion.

2. Description of the Prior Art

I.V. boards are widely used on children and adults to immobilize extremities and protect infusion sites. Their use is more important in children as they are more active and more likely to interfere with their I.V. Most I.V. boards are simply straight pieces of board with a plastic cover and a little padding in between. When a child's hand and lower arm are put on such a board, it needs to be strapped on and kept in place with a lot of tape. Removal of the tape after use tends to be uncomfortable, if not painful, since it sticks to the skin. Usually the boards are flat and therefore uncomfortable. They do not allow the hand to be put in the most advantageous position for starting an I.V. Veins stand out better and are more easily accessible when they are stretched by bending both wrist and fingers down. This is impossible to do with a conventional I.V. board. For this reason, doctors and nurses often start an I.V. without putting the hand on a board, so that the hand can be bent into the best position. After the procedure, the board is put on and the hand secured with tape. This is often a delicate and difficult undertaking, since it is easy to dislodge the intravenous needle. When an I.V. is difficult to start because subcutaneous fat makes it impossible to visualize a vein, a fiberoptic light source is used to transilluminate a hand to show up a vein. This is commonly referred to as a snake light because of its shape. This, too, has to be used before the hand is immobilized, causing the same problems of securing the I.V. afterwards. It is also difficult to hold the snake light in the hollow of the patient's hand and insert the needle into the vein at the same time.

This invention will solve all these problems. The shape of the I.V. board follows the natural curve of the hand and arm and is comfortable; it is sectioned in the middle to allow the wrist to be bent when the board is on; it requires no tape since it features a snap-on cover for the fingers and VELCRO-closing armbands, it provides an aperture through the center for the insertion of a snake light which will also stabilize the light, freeing the hands of the care provider to start the I.V.; it is quick and easy to use, immobilizing the hand with minimum effort.

SUMMARY OF THE INVENTION

The invention relates to an I.V. board that is made in two sections, a front part for the hand and a back part for the arm. This allows the front part to be put on separately, so that the hand can be bent down at the wrist, making it easier to visualize veins. The back part is added after the I.V. is started to immobilize the entire extremity. The board is held in place by an attached clear, plastic cover that snaps over the fingers and by armbands that are closed with VELCRO. Access for a snake light is provided through a hole in the front of the board and I.V. tubing can be secured by means of clips along the sides of the board.

DESCRIPTION OF THE PREFERRED EMBODIMENT

Figure 1:
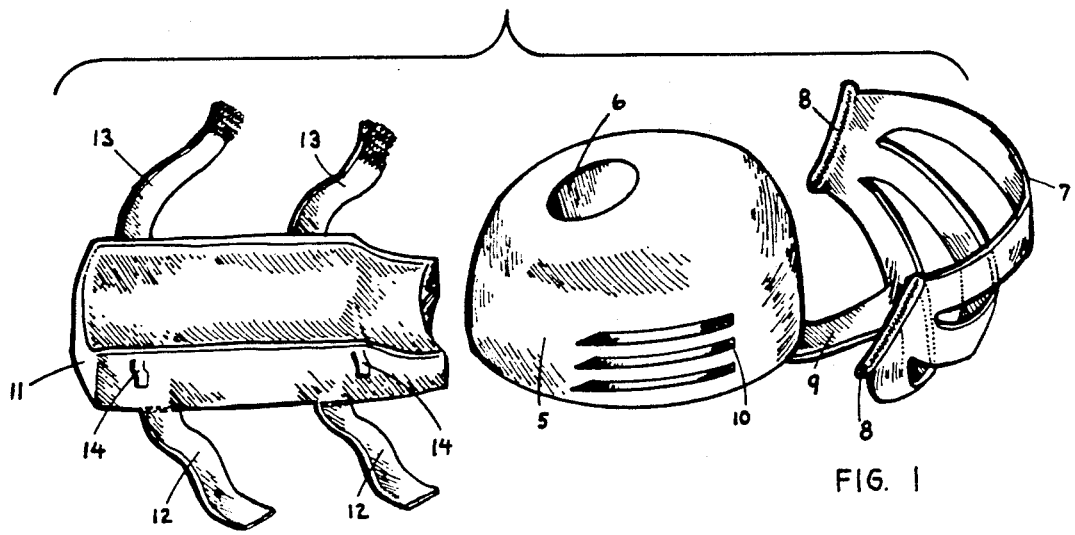
FIG. 1 is an elevational view of the sectioned I.V. board, showing both sections. The front or hand section has an attached cover for the fingers, the arm section features armbands with VELCRO closings.

Referring to FIG. 1, an embodiment of the invention is shown: an I.V. board consisting of two sections, a front board 5 to immobilize a patient's hand and a back board 11 to immobilize a patient's arm. The front board 5 is in the approximate shape of a half-globe with a slight upward slant and is made of rigid plastic. The top of the front board 5 shows a circular opening 6 that continues through to the bottom and that will allow the light beams from a snake light inserted from the bottom to exit at this point and transilluminate a hand that is placed over it. Attached to the front board 5 by a flexible band 9 is a cover 7, made of clear flexible plastic and consisting of three separate bands which are integrally joined at the edges and terminate in runners 8 of rigid plastic on both sides, the runners 8 having a rounded shape. When the cover 7 is put over a patient's hand, the bands of the cover 7 will fit over the knuckles and both finger joints respectively, while the runners B will snap into one of a set of three grooves 10 that are located on both sides of the front board 5. If the cover 7 needs tightening, one need only push it further down to let the runners 8 snap into the next lower groove 10. The runners 8 can also be adjusted horizontally within the grooves 10 to ensure a proper fit of the cover 7. The grooves 10 should be closed off at the fingertip end so that it becomes impossible to slide the cover 7 off. The back board 11 is shaped to the patient's arm for comfort and is also made of rigid plastic. Two sets of armbands 12 and 13 are attached to the side of the back board 11 one set to be located so that it will close over the patient's wrist and both sets having VELCRO closings. The back board 11 also shows clips 14 next to the armbands 12 and 13 which can be used to secure any I.V. tubing. These may be of any suitable shape or material.

Figure 2:
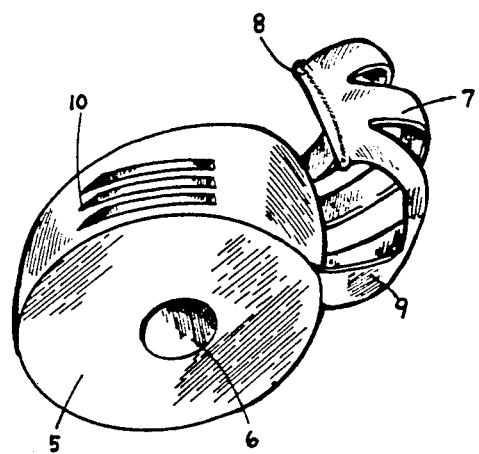
FIG. 2 is an elevational view of the front board shown from a different angle.

Referring to FIG. 2, a back view of the front board 5 is shown. The circular opening 6 is shown to start at the bottom of the board 5 and continues at a slight backward slant all the way through to the top. A fiberoptic light source would be inserted into the opening 6 from the bottom, so that the light can exit at the top.

Figure 3:
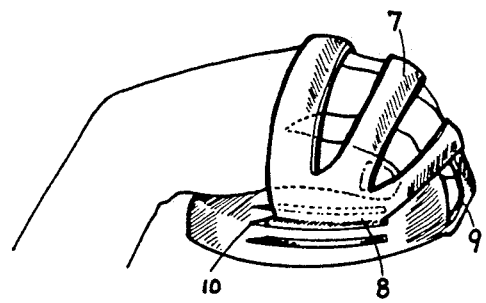
FIG. 3 is a side view of the front board in use, the patient's hand bent down at the wrist.

Referring to FIG. 3, a side view of the front board 5 is shown in use. The patient's hand is positioned over the board 5 with the cover 7 on, immobilizing the hand. The runners 8 are snapped into the middle one of the set of three grooves 10 on both sides of the front board 5. The patient's hand is bent down at the wrist in readiness for starting an I.V.

Figure 4:
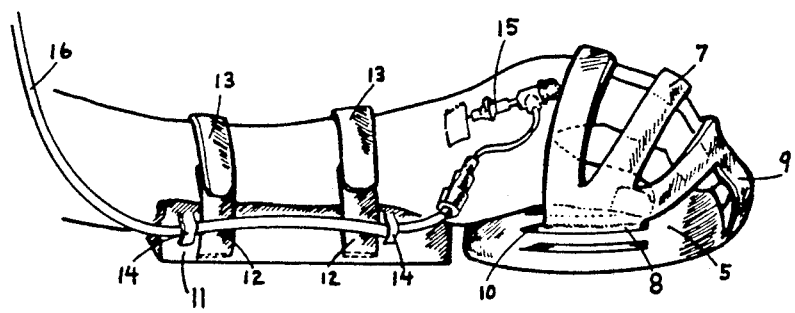
FIG. 4 is a side view of the whole board in use, showing the manner of attachment to hand and arm, the I.V. started and the I.V. tubing secured.

Referring to FIG. 4, both the front board 5 and the back board 11 are shown in use. The I.V. catheter 15 has been inserted and secured and the back board 11 added, which is immobilizing the arm by means of the two sets of arm bands 12 and 13. The I.V. tubing 16 is held in place by the clips 14 at the side of the back board 11.

Both sections of the I.V. board 5 and 11 are capable of being washed and autoclaved and are re-usable. They may be made in two or three different sizes to fit all ages of children. Suggested sizes would be small for ages 0–2, medium for ages 3–6 and large for ages 7–12.

Although embodiments of the invention are illustrated in the drawings and are previously described in detail, this invention encompasses also any configuration, design and relationship of components which will function in a similar manner and which will produce the equivalent results.

I claim:
1. A child's sectioned I.V. board comprising:
   (a) a hand section in the approximate shape of a half globe and made of rigid plastic;
   (b) a cover to immobilize a child's hand and made of clear, flexible plastic, molded to the shape of the hand and consisting of three separate bands integrally joined at the ends, these ends forming the sides of the cover;
   (c) runners of rounded rigid plastic attached to the sides of the cover;
   (d) a band made of flexible plastic that attaches the cover to the hand section of the I.V. board;
   (e) an arm section made of rigid plastic and molded to the shape of a child's arm and the heel of the hand;
   (f) two sets of arm bands attached to both sides of the arm section with closing means at the ends;
   (g) two sets of clips located next to the armbands on both sides of the arm section.

2. A sectioned I.V. board as recited in claim 1, in which the hand section has a circular opening in the center of the bottom which continues through to the top at a backward slant, and provides access for a light source, causing the light to exit where the palm of a child's hand would be located when in use, to illuminate the hand.

3. A sectioned I.V. board as recited in claim 2 in which the hand section has a set of three equidistant horizontal grooves on two sides of said globe into which the runners on the sides of the cover can be snapped, thus immobilizing a child's hand and permitting adjustment of the cover both vertically and horizontally.

4. A sectioned I.V. board as recited in claim 1, in which the arm bands are attached to the sides of the arm section so that that one set will close over the arm and the other over the child's wrist.

5. A sectioned I.V. board as recited in claim 4, in which the clips on both sides of the arm section are capable of securing I.V. tubing without damaging the tubing or inhibiting the flow of I.V. fluid.

* * * * *